US012661200B2

(12) United States Patent
Russell et al.

(10) Patent No.: US 12,661,200 B2
(45) Date of Patent: Jun. 23, 2026

(54) INTEGRATED ROBOTIC INSUFFLATION AND SMOKE EVACUATION

(71) Applicant: Verb Surgical Inc., Santa Clara, CA (US)

(72) Inventors: Geoffrey Robert Russell, San Jose, CA (US); Omar J. Vakharia, San Jose, CA (US); John H. Magnasco, San Jose, CA (US)

(73) Assignee: Auris Health, Inc., Santa Clara, CA (US)

( * ) Notice: Subject to any disclaimer, the term of this patent is extended or adjusted under 35 U.S.C. 154(b) by 90 days.

(21) Appl. No.: 18/789,573

(22) Filed: Jul. 30, 2024

(65) Prior Publication Data

US 2024/0415593 A1      Dec. 19, 2024

Related U.S. Application Data

(63) Continuation of application No. 17/725,387, filed on Apr. 20, 2022, now Pat. No. 12,097,004, which is a
(Continued)

(51) Int. Cl.
*A61B 34/00* (2016.01)
*A61B 17/00* (2006.01)
(Continued)

(52) U.S. Cl.
CPC ........ *A61B 34/71* (2016.02); *A61B 17/00234* (2013.01); *A61B 17/3421* (2013.01);
(Continued)

(58) Field of Classification Search
CPC .............. A61B 34/71; A61B 17/00234; A61B 17/3421; A61B 34/37; A61B 90/50;
(Continued)

(56) References Cited

U.S. PATENT DOCUMENTS 6,068,609 A    5/2000  Ott et al.
6,234,205 B1   5/2001  D'Amelio et al.
(Continued)

FOREIGN PATENT DOCUMENTS

CN      109788995 A     5/2019
EP        2279704 B1    12/2016
WO    2018/109595 A1     6/2018

OTHER PUBLICATIONS

AirSeal(registered) iFS Product Overview—ConMed—Accessed from the web on Oct. 3, 2019 at: https://www.conmed.com/en/medical-specialties/laparoscopic-robotic-and-opensurgery/general-and-bariatric-surgery/access/airseal-system/airseal-products/airseal-ifs-intelligent-flow-system.
(Continued)

*Primary Examiner* — Richard G Louis
(74) *Attorney, Agent, or Firm* — Aikin & Gallant, LLP

(57) ABSTRACT
A surgical robotic system comprising: a robotic arm; a tool drive coupled to the robotic arm; a cannula interface configured to couple a cannula to the tool drive, the cannula interface having a fluid pathway in communication with an interior lumen of the cannula; and an insufflation pathway coupled to the robotic arm, the insufflation pathway having a distal end coupled to the fluid pathway and a proximal end coupled to a surgical insufflator.

19 Claims, 11 Drawing Sheets

Related U.S. Application Data continuation of application No. 16/824,563, filed on Mar. 19, 2020, now Pat. No. 11,331,157.

(51) Int. Cl.

|  |  |
|---|---|
| *A61B 17/34* | (2006.01) |
| *A61B 34/37* | (2016.01) |
| *A61B 90/50* | (2016.01) |

(52) U.S. Cl.

CPC .............. *A61B 34/37* (2016.02); *A61B 90/50* (2016.02); *A61B 2017/3419* (2013.01); *A61B 2218/006* (2013.01); *A61B 2560/0456* (2013.01)

(58) Field of Classification Search

CPC ...... A61B 2017/3419; A61B 2218/006; A61B 2560/0456; A61B 34/35; A61B 2017/00477; A61B 2034/302; A61B 2218/001; A61B 2218/005; A61B 2218/008; A61B 34/30; A61B 2034/301; A61B 2217/005; A61B 2217/007

See application file for complete search history.

(56) References Cited

U.S. PATENT DOCUMENTS

| | | | |
|---|---|---|---|
| 8,715,219 | B2 | 5/2014 | Stearns et al. |
| 8,961,451 | B2 | 2/2015 | Stearns et al. |
| 9,155,557 | B2 | 10/2015 | Azarbarzin et al. |
| 9,526,886 | B2 | 12/2016 | Mastri et al. |
| 9,737,371 | B2 | 8/2017 | Romo et al. |
| 10,098,703 | B2 | 10/2018 | Radgowski et al. |
| 10,278,730 | B2 | 5/2019 | Norton et al. |
| 2007/0088275 | A1 | 4/2007 | Stearns et al. |
| 2009/0248039 | A1 | 10/2009 | Cooper et al. |
| 2011/0230723 | A1 | 9/2011 | Castro et al. |
| 2017/0050011 | A1 | 2/2017 | Zergiebel et al. |
| 2018/0132895 | A1* | 5/2018 | Silver ................ A61B 17/3421 |
| 2018/0168689 | A1* | 6/2018 | Beckman ........... A61B 17/3498 |
| 2018/0256204 | A1 | 9/2018 | Silver et al. |
| 2018/0256207 | A1 | 9/2018 | Augelli et al. |
| 2018/0310958 | A1 | 11/2018 | Silver et al. |
| 2019/0159825 | A1 | 5/2019 | Frampton et al. |
| 2019/0201036 | A1 | 7/2019 | Nott et al. |
| 2019/0201111 | A1 | 7/2019 | Shelton, IV et al. |
| 2020/0022766 | A1 | 1/2020 | Millman et al. |
| 2020/0405417 | A1 | 12/2020 | Shelton et al. |

OTHER PUBLICATIONS

Final Office Action for U.S. Appl. No. 16/824,563, mailed Nov. 10, 2021, 8 pages.

Final Office Action received for U.S. Appl. No. 17/725,387, mailed on Apr. 17, 2024, 7 pages.

Hahn et al., "Removal of Hazardous Surgical Smoke Usina a Built-in-FilterTrocar: A Study in Laparoscopic Rectal Resection.", Surgical Laparoscopy Endoscopy & Percutaneous Techniques, Oct. 2017, vol. 27, No. 5, pp. 341-345.

International Preliminary Report on Patentability for International Application No. PCT/US2020/032062 mailed Sep. 29, 2022, 11 pages.

International Search Report and Written Opinion dated Feb. 8, 2021, for related PCT Application No. PCT/US2020/032062.

MEGADYNE(trademark) MEGAVAC(trademark) Smoke Evacuator Product Data Sheet, Ethicon US, LLC., 2017.

Non-Final Office Action for U.S. Appl. No. 16/824,563, mailed May 13, 2021, 11 pages.

Non-Final Office Action received for U.S. Appl. No. 17/725,387, mailed on Dec. 7, 2023, 9 pages.

Notice of Allowance for U.S. Appl. No. 16/824,563, mailed Jan. 26, 2022, 7 pages.

Notice of Allowance of the U.S. Patent Office dated Jul. 18, 2024 for related U.S. Appl. No. 17/725,387.

Partial International Search Report & Provisional Opinion Accompanying the Partial Search Result, dated Dec. 1, 2020, for related PCT Application No. PCT/US2020/032062. 8 pages.

PneumoClear Insufflator—Product Data Sheet, Stryker, Apr. 2018, Available Online at: <https://www.stryker.com/us/en/endoscopy/products/pneumoclear.html>.

Office Action received for Korean Application No. 10-2022-7036184, mailed on Jul. 25, 2025, 6 pages (4 pages of original office action and 2 pages of English Translation).

First Office Action received for Chinese Patent Application No. 202080098877.2, mailed on Jun. 19, 2025, 27 pages (11 pages of Original Document and 16 pages of English Translation).

Extended European Search Report received for EP Patent Application No. 25216748.1, mailed Feb. 12, 2026, 11 pages.

\* cited by examiner

INTEGRATED ROBOTIC INSUFFLATION AND SMOKE EVACUATION

CROSS-REFERENCE TO RELATED APPLICATION

This application is a continuation of co-pending U.S. patent application Ser. No. 17/725,387, filed Apr. 20, 2022, which is a continuation of U.S. patent application Ser. No. 16/824,563, filed Mar. 19, 2020, now U.S. Pat. No. 11,331, 157, issued May 17, 2022, which is incorporated by reference herein.

FIELD

Embodiments related surgical robotic systems, are disclosed. More particularly, embodiments related to a surgical robotic arm with a fluid pathway integrated into the tool drive-cannula interface for insufflation and smoke evacuation, are disclosed.

BACKGROUND

Minimally-invasive surgery (MIS), such as endoscopic surgery, involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools. Access may be provided to the body cavity of a patient through a trocar. Once a distal end of a cannula of the trocar is properly positioned and inserted through tissue and into an interior region of the patient, for example, through the abdominal wall of the patient, a surgical robotic arm having a trocar docking interface at its distal end, or a tool drive attached thereto, is manually maneuvered by a user until the docking interface is aligned with an attachment portion (e.g., a mating cannula interface) on the proximal end of the trocar (outside the patient.) The user then latches the components to each other, either manually or as an automated step, thereby rigidly attaching the arm to the trocar. A surgical tool having an end effector at its distal end (e.g., scissors, grasping jaws, or camera) is then inserted into a top opening of the cannula and the tool is then attached to the arm such that further surgical operations can be performed with the tool.

SUMMARY

Smoke is a common complaint in MIS because it obstructs visualization of the anatomy and makes performing surgical tasks difficult. In some cases, to address this issue, a surgical insufflator and/or smoke evacuation system may be used in addition to the surgical system components. The use of a separate insufflator and/or smoke evacuation system, however, increases procedural time and workflow difficulties resulting in higher costs for the hospital. The instant invention proposes a robotic arm with fluid pathways (e.g., insufflation tubing) integrated into components of the surgical system, for example, the surgical robotic arm and an interface between the tool drive and a cannula coupled to the tool drive. The fluid pathway and/or insufflation tubing is coupled to a pump (e.g., surgical insufflator) that can be used to control a flow of gas to/from the surgical site within which the cannula is positioned. The integrated pathways eliminate additional workflow operations (e.g., configuration of separate insufflation tubing) and improve user workflow and smoke evacuation, allowing for significantly improved surgical site visualization and improved intraoperative performance.

Representatively, the overall system may include a robotic arm and a cannula interface (e.g., at a proximal end of the trocar) used to rigidly attach a cannula to a tool drive coupled to the robotic arm. A fluid pathway (e.g., port, tube, lumen, channel, or the like) that allows for transmission of a fluid (e.g., insufflation gas) along the robotic arm, and directly to the cannula, is further integrated into the system. The integrated pathway may include, for example, an insufflation tube that is attached at one end to a surgical insufflator (e.g., a pump for controlling gas flow to/from the surgical site) and extends along the arm housing to the cannula interface. The end of the insufflation tube at the cannula interface side may be attached to a portion of the integrated pathway formed through the cannula interface to the cannula lumen. In this way, a flow of fluid may be transmitted from the surgical insufflator to the surgical site within which the cannula is positioned, without having to attach a separate insufflation component to the surgical robotic system. In addition, the direction of fluid flow may be reversed and the insufflation tube may be used to evacuate smoke from the surgical site. In still further aspects, there may be more than one insufflation tube and/or fluid pathways formed within the cannula interface to facilitate gas transmission as desired. In some cases, the insufflation tube and/or pathway may be coupled to a valve that enables the flow of fluid to be stopped as desired. In addition, in some aspects instead of directly integrating the insufflation tubing into the robotic arm, the insufflation tubing could be combined with a sterile drape. The surgical insufflator could also be integrated into the overall robotic system.

Additional configurations may include modes that dynamically adjust fluid inflow and outflow from each cannula of the system to address various surgical conditions. For example, the system may include a processor configured to detect when a compatible energy device is activated and then increase fluid outflow from the surgical site to remove smoke and particulate while simultaneously increasing inflow to prevent loss of pneumoperitoneum. To address fogging, the system could dynamically switch which pathway or port has insufflation/smoke evacuation to move a flow of gas away from the endoscope. In addition, the system may include a heating element, for example incorporated within the insufflation tubing, and a flow of heated gas could be switched to the cannula with the endoscope to warm it and remove the fog. Still further, if particulate is detected on the endoscope or a camera, the system could increase a fluid outflow to the endoscope or camera to blow particulate away from the instrument.

Representatively, in one aspect, a surgical robotic system includes a robotic arm; a tool drive coupled to the robotic arm; a cannula interface configured to couple a cannula to the tool drive, the cannula interface having a fluid pathway in communication with an interior lumen of the cannula; and an insufflation pathway coupled to the robotic arm, the insufflation pathway having a distal end coupled to the fluid pathway and a proximal end coupled to a surgical insufflator. The fluid pathway may be integrated within the cannula interface and dimensioned to allow transmission of an insufflation gas between the insufflation pathway and the interior lumen of the cannula. The tool drive may include a docking interface and the insufflation pathway may be coupled to the docking interface. The interior lumen of the cannula may be dimensioned to receive a surgical tool.

The system may further include a filter in communication with the fluid pathway such that an insufflation gas transmitted through the insufflation pathway to the fluid pathway passes through the filter. The filter may be integrated into a sterile adapter positioned between the tool drive and the cannula interface. A sealing element may further be integrated into the sterile adapter to seal the filter between the tool drive and the cannula interface and prevent leakage of the insufflation gas.

In some aspects, the fluid pathway may be a first fluid pathway and the insufflation pathway is a first insufflation pathway, and the surgical robotic system may also include a second fluid pathway coupled to a second insufflation pathway. In some aspects, a valve is coupled to at least one of the first fluid pathway or the second fluid pathway to control a flow of a fluid through the first fluid pathway or the second fluid pathway. Still further, a nozzle may be coupled to the fluid pathway, and the nozzle may be configured to direct an insufflation gas flowing through the fluid pathway toward a surgical instrument positioned within the interior lumen of the cannula. The insufflation pathway may be an insufflation tube. The insufflation tube may be enclosed within an outer shell of the robotic arm. The insufflation tube may be mechanically attached to an outer surface of an outer shell of the robotic arm.

In another aspect, a surgical robotic system includes a surgical robotic assembly having a robotic arm, a tool drive and a cannula interface for coupling a cannula to the tool drive, the cannula interface having a fluid pathway integrated therein that is in fluid communication with an interior lumen of the cannula; an insufflation tube coupled to the robotic arm, the insufflation tube having a distal end coupled to the fluid pathway and a proximal end coupled to a surgical insufflator; and a processor communicatively coupled to the surgical robotic assembly and the surgical insufflator, the processor operable to control an operation of the surgical insufflator based on a detected surgical condition. In some aspects, the detected surgical condition is a presence of smoke within a surgical site; and the operation controlled by the processor is a smoke evacuation function of the surgical insufflator. The smoke evacuation function may include actively evacuating smoke through the insufflation tube while maintaining pneumoperitoneum at the surgical site. In some aspects, the fluid pathway is a first fluid pathway and the insufflation tube is a first insufflation tube, and the surgical robotic assembly further comprises a second fluid pathway and a second insufflation tube that are not fluidly coupled to the surgical insufflator, and the smoke evacuation function comprise passively evacuating smoke through the second fluid pathway and second insufflation tube. In still further aspects, the robotic arm is a first robotic arm and the insufflation tube is a first insufflation tube, the system further comprising a second robotic arm and a second insufflation tube integrated with the second robotic arm, and the smoke evacuation function comprises introducing a flow of fluid to the surgical cavity through the first insufflation tube and evacuating smoke from the surgical cavity using the second insufflation tube. In some cases, the detected surgical condition may be activation of an energy device within a surgical site; and the operation controlled by the processor is a smoke evacuation function of the surgical insufflator. In other aspects, the detected surgical condition may be a presence of particles within a surgical site; and the operation controlled by the processor is a particle removal function of the surgical insufflator.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
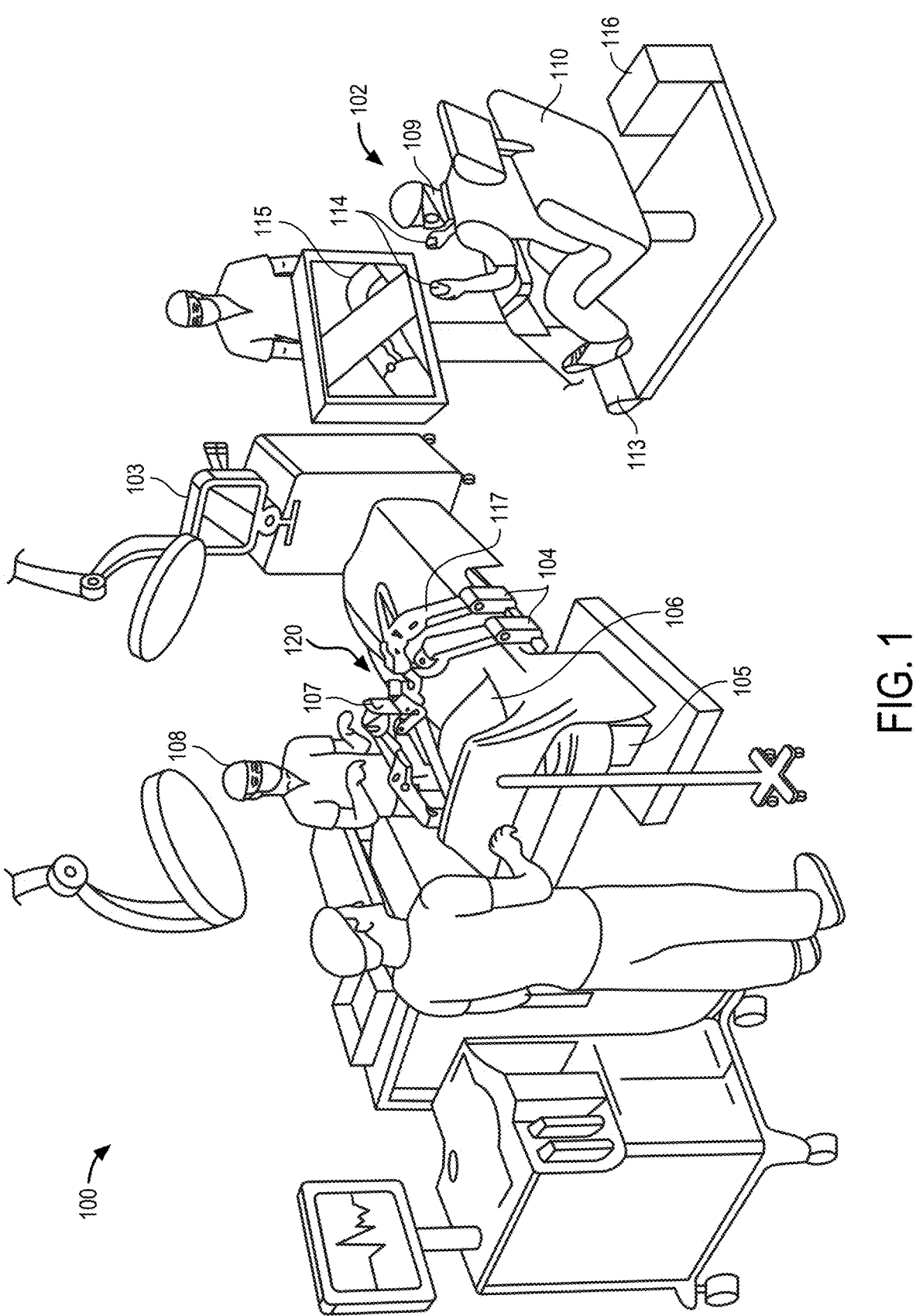
FIG. 1 is a pictorial view of an example surgical robotic system in an operating arena, in accordance with an embodiment.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for case of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The surgical robotic arms 104 are shown as a table-mounted system, but in other configurations the surgical robotic arms 104 may be mounted in a cart, ceiling or sidewall, or in another suitable structural support.

Generally, a remote operator 109, such as a surgeon or other operator, may use the user console 102 to remotely manipulate the surgical robotic arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

Figure 2:
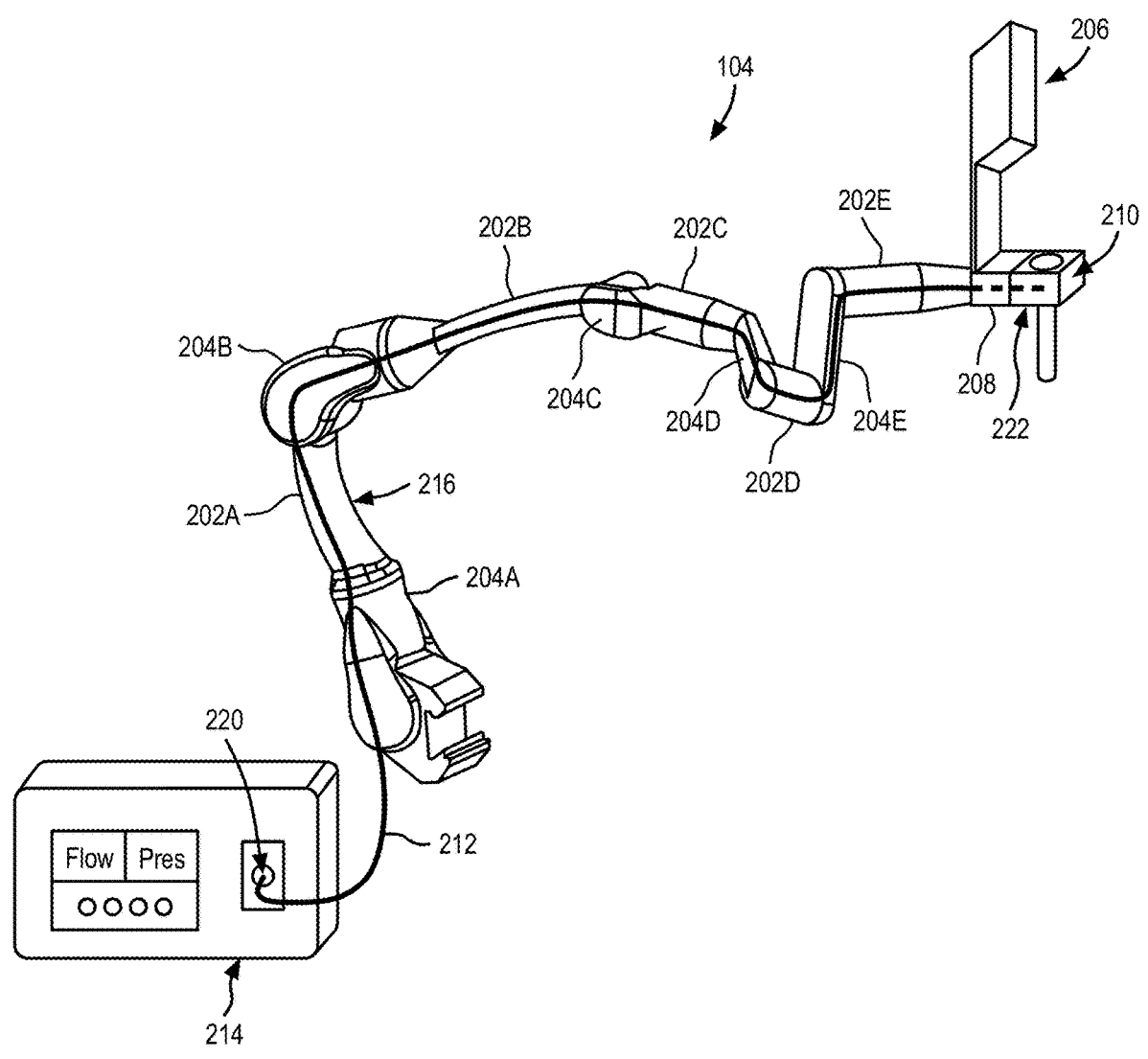
FIG. 2 is a perspective view of a portion of a robotic arm according to one aspect of the disclosure.

Turning to FIG. 2, a portion of a robotic arm 104 is illustrated according to one aspect of the disclosure. The robotic arm 104 and associated components described herein can form a surgical robotic system according to an embodiment of the disclosure. The robotic arm 104 can be incorporated into the surgical robotic system 100 described in reference to FIG. 1, or can form a portion of a different system. While a single robotic arm 104 is illustrated, it will be understood that the robotic arm 104 can include additional arm portions or can be a component of a multi-arm apparatus without departing from the disclosure.

The robotic arm 104 may include a plurality of links (e.g., links 202A-202E) and a plurality of joint modules (e.g., joints 204A-204E) for actuating the plurality of links relative to one another. The joint modules can include various joint types, such as a pitch joint or a roll joint, any of which can be actuated manually or by the robotic arm actuators 117, and any of which may substantially constrain the movement of the adjacent links around certain axes relative to others. As also shown, a tool drive 206 is attached to the distal end of the robotic arm 104. As described herein, the tool drive 206 can be configured with a docking interface 208 to receive an attachment portion (e.g., a mating cannula interface at a proximal end of the trocar) of a trocar 210 such that one or more surgical instruments (e.g., endoscopes, staplers, etc.) can be guided through a lumen of the cannula of the trocar 210. The plurality of the joint modules 204A-204E of the robotic arm 104 can be actuated to position and orient the tool drive 206 for robotic surgeries.

A fluid pathway 212 for controlling a flow of fluid to/from a surgical site or surgical cavity within which the trocar 210 is positioned, is also shown. The fluid pathway 212 may be integrated with, attached to, or otherwise formed as part of, the robotic arm 104. The fluid pathway 212 may be coupled to a pump assembly 214, for example an insufflation pump, and therefore also be referred to herein as an insufflation pathway. For example, at least a portion of the fluid pathway 212 may be an insufflation tube (e.g., insufflation pathway) that is connected to the pump 214 and runs along an entire length of the robotic arm 104. The insufflation tube may be enclosed within the cosmetic panels 216 forming the arm 104. For example, the insufflation tube may be mechanically attached (e.g., clamp, clip, bolt, bracket, fastener, or the like) to an inner surface of the panels 216, or may be positioned within tube receiving channels formed within the inner surface of the panels 216. Alternatively, the insufflation tube may be connected to an exterior surface of the panels 216 forming the arm 104. For example, the insufflation tube may be mechanically attached to the exterior surface by bands, ties, or the like. A proximal end 220 of fluid pathway 212 may be attached to the pump assembly 214, for example a surgical insufflator, that controls the flow of fluid through the pathway 212. A distal end 222 of the fluid pathway 212 may be attached to the cannula associated with the trocar 210. The pump assembly 214 may control the direction of fluid flow through the pathway 212 to allow for smoke evacuation, particulate removal, pneumoperitoneum, or management of other conditions within the associated surgical site or surgical cavity during the surgical procedure.

Figure 3:
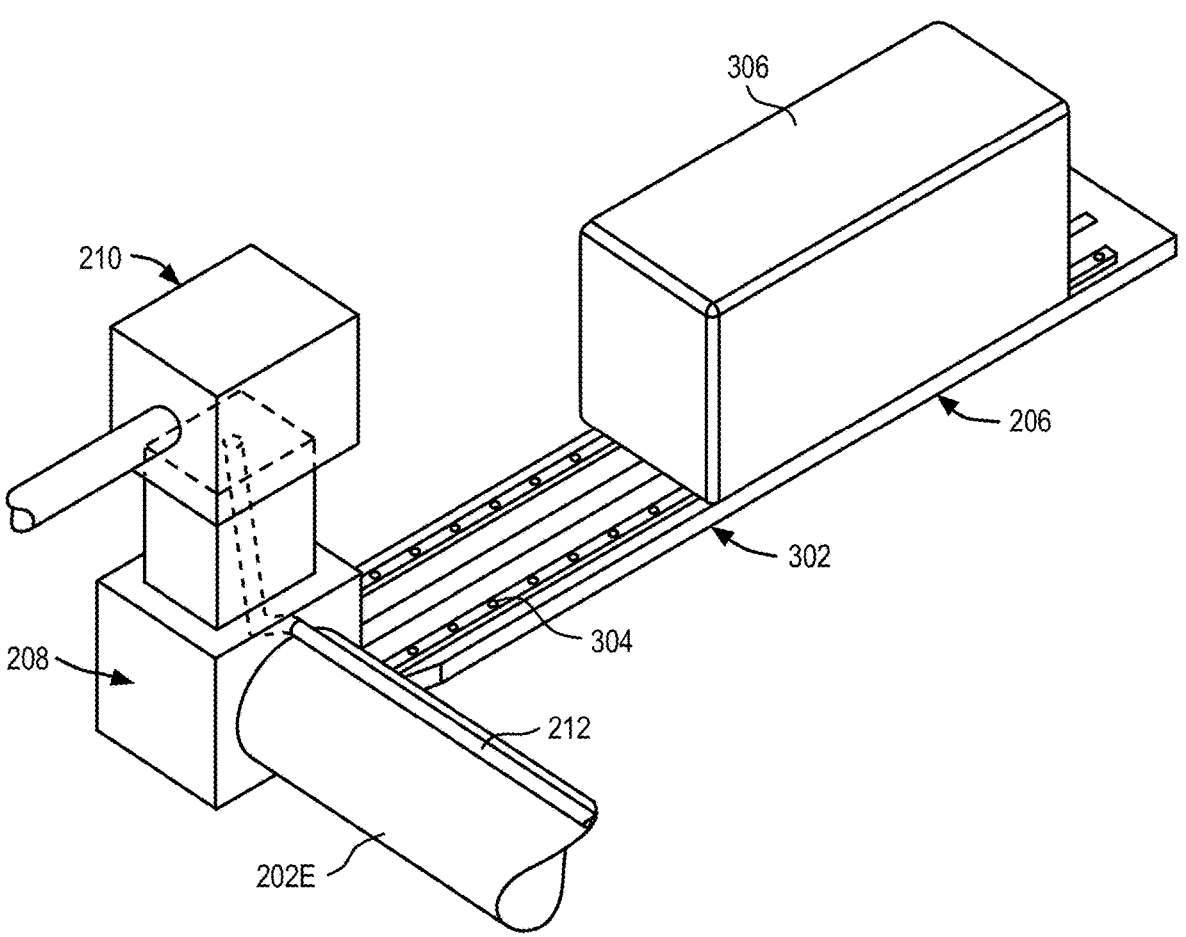
FIG. 3 is a schematic perspective view of a tool drive of the robotic arm of FIG. 2.

FIG. 3 is a schematic diagram illustrating an exemplary tool drive 206 without a loaded tool in accordance with aspects of the subject technology. In one variation, the tool drive 206 may include an elongated base (or "stage") 302 having longitudinal tracks 304 and a tool carriage 306, which is slidingly engaged with the longitudinal tracks 304. The stage 302 may be configured to couple to the distal end of a robotic arm 104 (see FIG. 2) such that articulation of the robotic arm 104 positions and/or orients the tool drive 206 in space. The tool carriage 306 may be configured to receive a tool that extends through the trocar 210.

Additionally, the tool carriage 306 may actuate a set of articulated movements through a cable system or wires manipulated and controlled by actuated drives (the terms "cable" and "wire" are used interchangeably throughout this application). The tool carriage 306 may include different configurations of actuated drives, such as a mechanical transmission. The trocar 210 can be coupled to the tool drive 206, or another component of the surgical robotic system 100, at a docking station or docking interface 208 located at a distal block of the elongated base 302. The docking interface 208 is configured to receive a portion of the trocar 210 such that the docking interface 208 is configured as a trocar docking interface, a trocar attachment device, or a trocar mounting device. The docking interface 208 can provide a reliable and quick way to attach the trocar 210 to the surgical robotic system 100. For example, although not shown, the docking interface 208 can define a receiving space for receiving a portion of the trocar 210 (e.g., a cannula interface at a proximal end of trocar). Once in position, the docking interface 208 and trocar 210 may be held in place relative to one another using a clamping assembly. In some variations, the docking interface 208 may also provide a sterile barrier between sterile components such as the trocar 210 and non-sterile components on the other side of the docking interface. The sterile barrier may be provided, for example, by a sterile adapter formed of a surgical-grade polymer or other surgical-grade material that is interposed between the trocar 210 and the docking interface 208 (as will be described in more detail in reference to FIG. 4).

Figure 4:
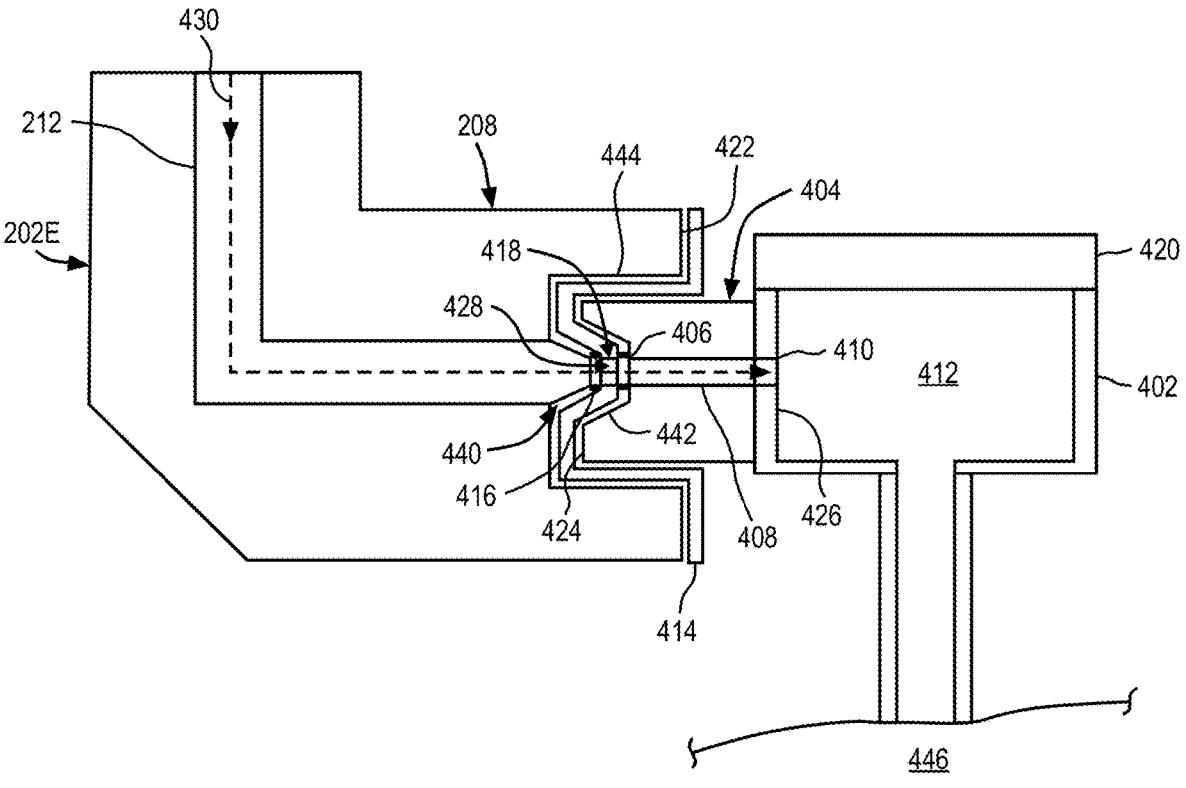
FIG. 4 is a cross-sectional side view of a tool drive and a cannula associated with the trocar of FIG. 3.

In addition, it can further be seen from this view that the fluid pathway 212 extends along the robotic arm link 202E (e.g., attached to the interior or exterior surface of the link panel) to the docking interface 208. The distal end of the fluid pathway 212 is further shown directly connecting to a cannula of the trocar 210, as will now be described in more detail in reference to FIG. 4. Representatively, FIG. 4 is a cross-sectional side view of the interface between the tool drive and a cannula of the trocar assembly described in FIG. 3. From this view, it can be seen that pathway 212 is integrated into robotic arm link 202E and docking interface 208. For example, pathway 212 may be formed by an insufflation tube mounted to, or integrally formed with, the exterior and/or interior surface of link 202E and docking interface 208. It is further contemplated that, in some aspects, at least a portion of pathway 212 may be a channel formed through link 202E and/or interface 208, that allows for fluid transmission alone, or in combination with, for example, an insufflation tube. The portion of pathway 212 directly coupled to link 202E may terminate at a distal end or portion 422 of docking interface 208.

A cannula 402 (with the remaining trocar components removed for case of illustration) is further shown including a cannula interface 404, which is received by docking interface 208, to secure the two components together. Cannula interface 404 may be a protruding or extended portion (e.g. a lug) of cannula 402 (e.g., located at a proximal end of the trocar) that is suitable for insertion within a receiving portion or cavity 414 formed in the distal end of docking interface 208. The cannula interface 404 includes an integrated fluid pathway 408 (e.g., a cannula side pathway) that connects the fluid pathway 212 (e.g., the tool drive side pathway) to the cannula 402. Representatively, cannula interface 404 may include pathway 408 formed by a channel within interface 404. The channel may extend between a fluid port 406 (e.g., tool drive side port) at a proximal end 424 of the cannula interface 404 and a fluid port 410 (e.g., cannula side port) at a distal end 426 of the cannula interface 404. Fluid port 410 opens to the lumen 412 of cannula 402 and fluid port 406 opens to an external environment surrounding the cannula. When cannula interface 404 is engaged with the docking interface 208, fluid port 406 becomes aligned with, and fluidly coupled to, the pathway 212 (e.g. on the tool drive side) such that a fluid (e.g., insufflation gas) can travel along pathways 212, 408 to/from the lumen 412 of cannula 402, as shown by arrow 430. The lumen 412 of cannula 402 extends to the surgical site or cavity so that the fluid traveling through pathways 212, 408 is transmitted to/from the cavity depending on the desired operation (e.g., insufflation, smoke evacuation, particular removal, etc). It can further be understood from this view that the integrated pathways 212, 408 may be in communication with the same cannula lumen 412 within which a surgical tool may be positioned. In other words, a fluid(s) traveling between pathways 212, 408 and the surgical cavity may use a same pathway as the surgical tool, as opposed to forming a separate pathway through the cannula 402.

In some aspects, a sterile adapter 414 may be positioned between cannula interface 404 and docking interface 208 to create a sterile barrier around cannula 402. The sterile adapter 414 may include an adapter opening 428 that is aligned with the pathways 212, 408, when cannula interface 404 is connected with docking interface 208, to allow for the transmission of fluid to the cannula 402, as previously discussed. A filter 428 could further be positioned between cannula interface 404 and docking interface 208. For example, filter 428 could be part of, or otherwise coupled to, sterile adapter 414. Filter 428 may be in communication with pathways 212, 408 so that it filters the fluid transmitted through pathways 212, 408. For example, filter 428 could be a filter which blocks particulates or other non-sterile matter from the surgical cavity from contaminating the pathway 212 so that the robotic side of the pathway (e.g., insufflation tubing) can be used for an entire day of procedures and only the adapter 414 and cannula 402 need to be replaced between patients. In addition, a seal 416 for sealing the adapter 414 and/or filter 428 between the docking and cannula interfaces 208, 404 may further be provided. For example, the seal 416 may be an o-ring or similar type structure that is coupled to the adapter opening 428 and integrated within, or otherwise forms part of, the sterile adapter 414.

In still further aspects, it is contemplated that an optional nozzle 440 may further be provided to control and/or direct a fluid flow through pathways 212, 408. For example, nozzle 440 may be formed at the docking and cannula interface 208, 404. Representatively, nozzle 440 may be a protruding portion or spout that is formed at the distal end 422 of docking interface 208 and/or pathway 212. The proximal end of cannula interface 404, which engages docking interface 208, may have recessed portion 442 that is dimensioned to receive nozzle 440 therein. The nozzle 440 may be used to stop the flow of an insufflation gas through pathway 212 of docking interface 208 to pathway 408 of cannula interface 408. Nozzle 440 may be integrally formed with pathway 212, or a separate piece attached to pathway 212. Nozzle 440 may have any shape, size and/or configuration suitable for controlling and/or directing a flow of fluid through pathways 212, 408.

Figure 5:
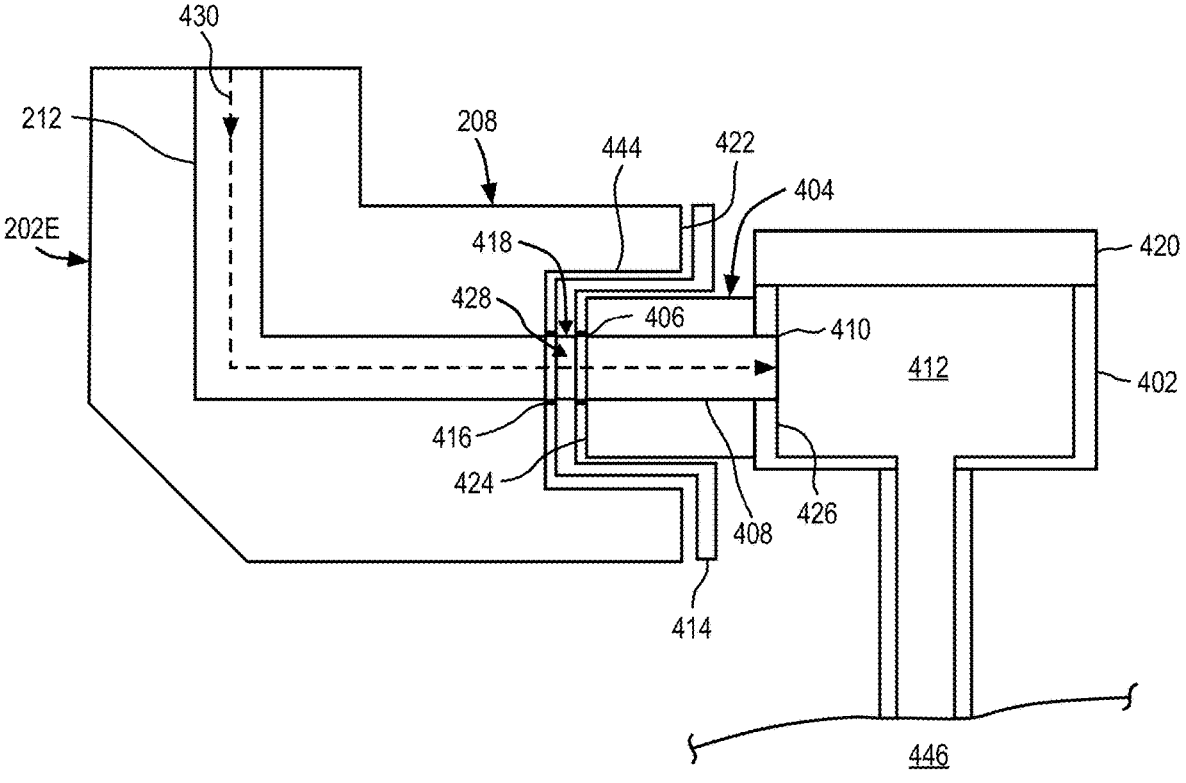
FIG. 5 is a cross-sectional side view of a tool drive and a cannula associated with the trocar of FIG. 3.

In other aspects, nozzle 440 may be omitted. Representatively, FIG. 5 shows a configuration in which the nozzle is omitted and the interface 208 and cannula interface 404 are substantially flat. Representatively, FIG. 5 is a cross-sectional side view of the robotic arm link 202E, docking interface and cannula 402 of FIG. 4, except that the interfacing sides of docking interface 208 and cannula interface 404 are flat, planar, or otherwise flush, with one another and nozzle 440 is omitted. The remaining components of the tool drive and cannula interface of FIG. 5 are the same as those described in reference to FIG. 4.

Returning now to FIG. 4, additional aspects of cannula 402 may include a cannula seal 420. The cannula seal 420 may seal the cannula lumen 412 from the ambient environment so that the fluid flow in/out of the cannula lumen 412 is prevented from entering the ambient environment. Cannula seal 420 may, however, allow for a surgical tool to be inserted into cannula 402, and once inserted, may seal around the tool so that the fluid does not leak around the tool. For example, cannula seal 420 may include a valve which allows for the insertion and/or removal of a surgical tool but will not open in response to a pressure from the fluid being transmitted in/out of the cannula lumen 412.

Figure 6:
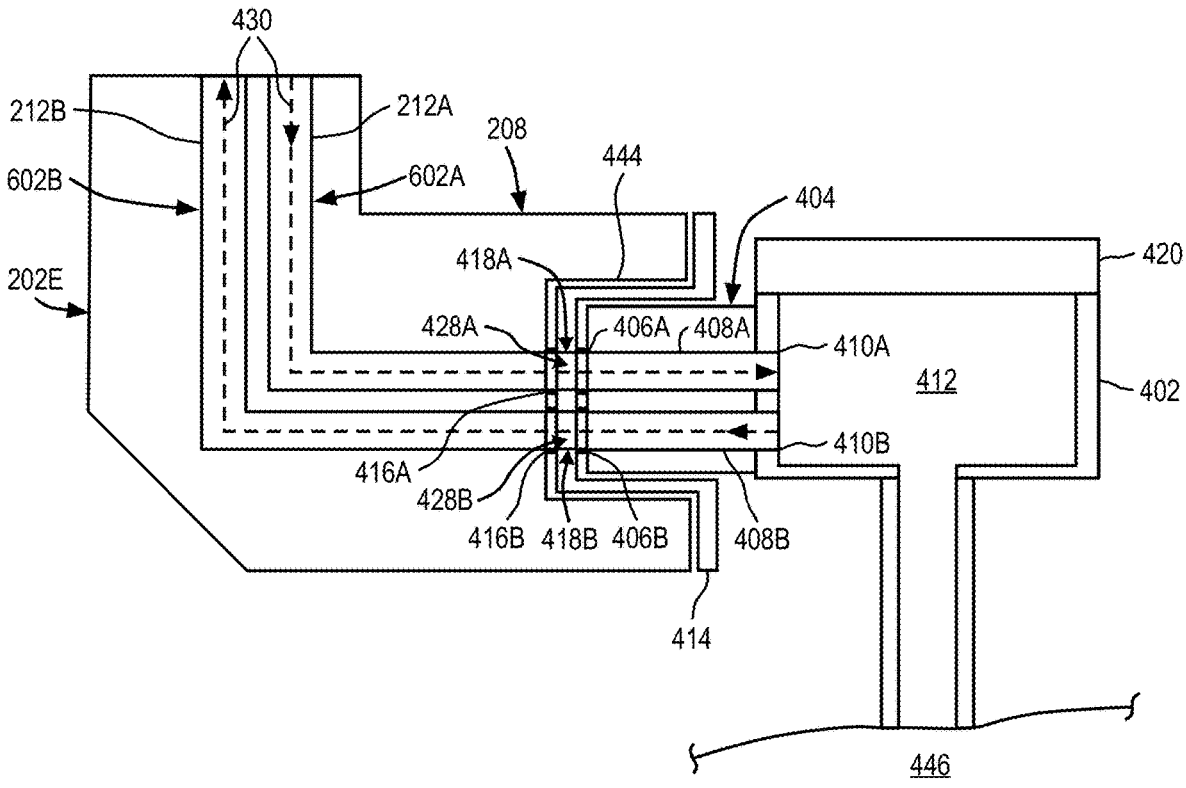
FIG. 6 is a cross-sectional side view of a tool drive and a cannula associated with the trocar of FIG. 3.

FIG. 6 is a cross-sectional side view of a tool drive and cannula interface according to another aspect of the invention. The tool drive and cannula interface of FIG. 6 is substantially similar to that of FIGS. 4-5 in that it includes a robotic arm link 202E and docking interface 208 that connects with, or interfaces with, the cannula interface 404 of cannula 402 as previously discussed. In this aspect, however, the assembly includes two integrated fluid pathways 602A, 602B for input/output of a fluid between the pump (not shown) and cannula 402. In particular, the assembly includes a first fluid pathway 602A which includes a fluid pathway 212A integrated with the robotic arm link 202E and docking interface 208 (e.g., the tool drive side pathway) and fluid pathway 408A integrated with the cannula interface 404 (e.g., the cannula side pathway). Fluid pathway 408A extends between a fluid port 406A at a proximal end of the cannula interface 404 and a fluid port 410A at a distal end of the cannula interface 404. Fluid port 406A is in fluid communication with the fluid pathway 212A while fluid port 410A is in fluid communication with the cannula lumen 412. In this aspect, fluid can travel along pathways 212A, 408A to/from the surgical cavity 446, as previously discussed. The assembly further includes a second fluid pathway 602B which is separate from the first pathway and includes fluid pathway 212B integrated with the robotic arm link 202E and docking interface 208 (e.g., the tool drive side pathway) and fluid pathway 408B integrated with the cannula interface 404 (e.g., the cannula side pathway). Fluid pathway 408B extends between a fluid port 406B at a proximal end of the cannula interface 404 and a fluid port 410B at a distal end of the cannula interface 404. Fluid port 406B is in fluid communication with the fluid pathway 212B while fluid port 410B is in fluid communication with the cannula lumen 412. In this aspect, a fluid can travel along pathways 212B, 408B to/from the surgical cavity 446, as previously discussed. Pathways 602A and 602B may run substantially parallel to one another as shown, or may be in any other configurations which allow for separate and independent fluid transmission into and/or out of the associated surgical cavity 446.

In the illustrated configuration, pathways 602A and 602B are completely separate pathways which allow for different fluids (e.g., a first fluid and a second fluid) or the same fluid to travel to/from the surgical cavity 446. The fluid(s) may travel in the same or different directions, as desired. For example, the first pathway 602A can be used for maintaining insufflation within surgical cavity 446 and pathway 602B can be used for smoke evacuation from surgical cavity 446. Representatively, insufflation gas from an associated surgical insufflator (e.g., insufflator 214 shown in FIG. 2) may flow through the first pathway 602A in a direction toward cannula 402 (as shown by dashed arrows) for delivery to the surgical cavity 446. A fluid may also flow through the second pathway 602B in the opposite direction (as shown by dashed arrows) to remove the gas, smoke and/or any other fluids or particulates from the cavity 446. In this aspect, the first and second pathway 602A-B can be used for active insufflation and smoke and/or particulate evacuation. These operations are considered "active" in that the pump (e.g., surgical insufflator 214) which is connected to both pathways, can be used to drive the direction of fluid flow. These operations may be performed simultaneously, consecutively, or at other time, as desired, as will be discussed in more detail in reference to FIG. 10.

In addition, a sterile adapter 414, similar to the sterile adapter previously discussed in FIG. 4-FIG. 5, may be positioned between cannula interface 404 and docking interface 208 to create a sterile barrier around cannula 402. In this configuration, however, the sterile adapter 414 may include first and second adapter openings 418A, 418B to accommodate the first and second pathways 212A-B, 408A-B and allow for the transmission of fluid along both pathways to the cannula 402, as previously discussed. Filters 428A, 428B may also be positioned between cannula interface 404 and docking interface 208. Filter 428A may be in communication with pathways 212A, 408A and filter fluids transmitted through pathways 212A, 408A. Filter 428B may be in communication with pathways 212B, 408B and filter fluid transmitted through pathways 212B, 408B. One or both of filter 428A-B could be filters which block fluids or particulates from being transferred between pathways 212A-B and pathways 408A-408B. For example, filter 428B, which is associated with second pathway 602B, shown in this configuration as transmitting fluids away from the surgical cavity 446 (see arrow), could be a filter which blocks particulates or other non-sterile matter retrieved from the surgical cavity from being transmitted from pathway 408B to pathway 212B. This configuration allow the robotic side of the pathway (e.g., insufflation tubing) to be used for an entire day of procedures and only the adapter 414 and cannula 402 need to be replaced between patients. In addition, seals 416A, 416B for scaling the adapter 414 and/or filters 428A-B between the docking and cannula interfaces 208, 404 may further be provided. It is further contemplated that although not shown in FIG. 6, one or both of pathways 602A-B may include a nozzle such as the nozzle 440 previously discussed in reference to FIG. 4.

Figure 7:
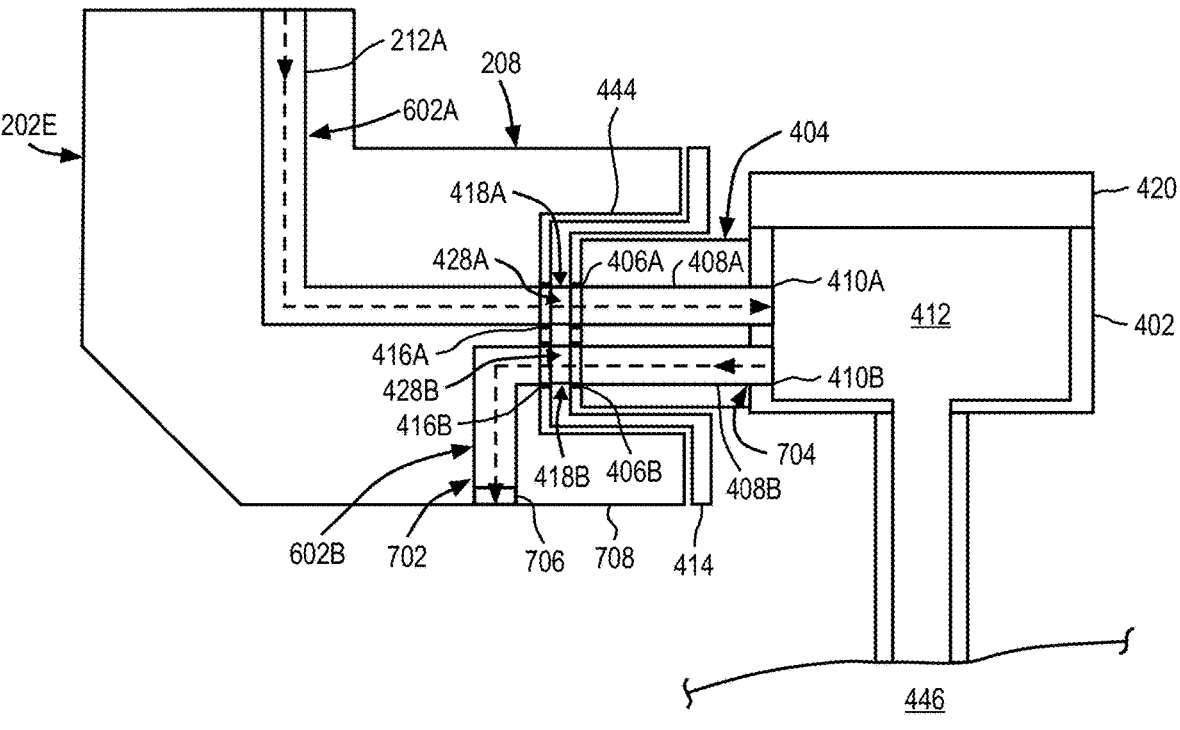
FIG. 7 is a cross-sectional side view of a tool drive and a cannula associated with the trocar of FIG. 3.

FIG. 7 is a cross-sectional side view of a tool drive and cannula interface according to another aspect of the invention. The tool drive and cannula interface of FIG. 7 is substantially similar to that of FIG. 6 in that it includes a robotic arm link 202E and docking interface 208 that connects with, or interfaces with, the cannula interface 404 of cannula 402 as previously discussed. In addition, the assembly includes two integrated fluid pathways 602A, 602B for input/output of a fluid between the pump (not shown) and cannula 402, and a sterile adapter 414 including filters 418A-B, as previously discussed. In this configuration, however, the first pathway 602A extends along the robotic arm to the pump (as shown in FIG. 2), while the second pathway 602B does not extend the entire length of the robotic arm to the pump. Rather, second pathway 602B extends out the side of the interface 404. Representatively, pathway 602B may have a distal end 704 connected to cannula lumen 412 and a proximal end 702 that terminates at the docking interface 208. The proximal end 702 of the pathway 602B may terminate at, or near, a side 708 of docking interface 208 (instead of the proximal end of the robotic arm 104), and be open to the ambient environment. A valve 706 may further be connected to the proximal end 702 of pathway 602B to open and close the end, and control the transmission of fluid between pathway 602B and the ambient environment. The pathways 602A, 602B can be used for insufflation and/or smoke evacuation similar to the pathways described in FIG. 6, except this configuration allows for passive smoke evacuation through pathway 602B. The operation is considered "passive" in that at least one of the pathways, namely pathway 602B, is not connected to the pump (e.g., surgical insufflator 214) and therefore fluid flow through this pathway is not directly driven, or otherwise controlled, by the pump.

Figure 8:
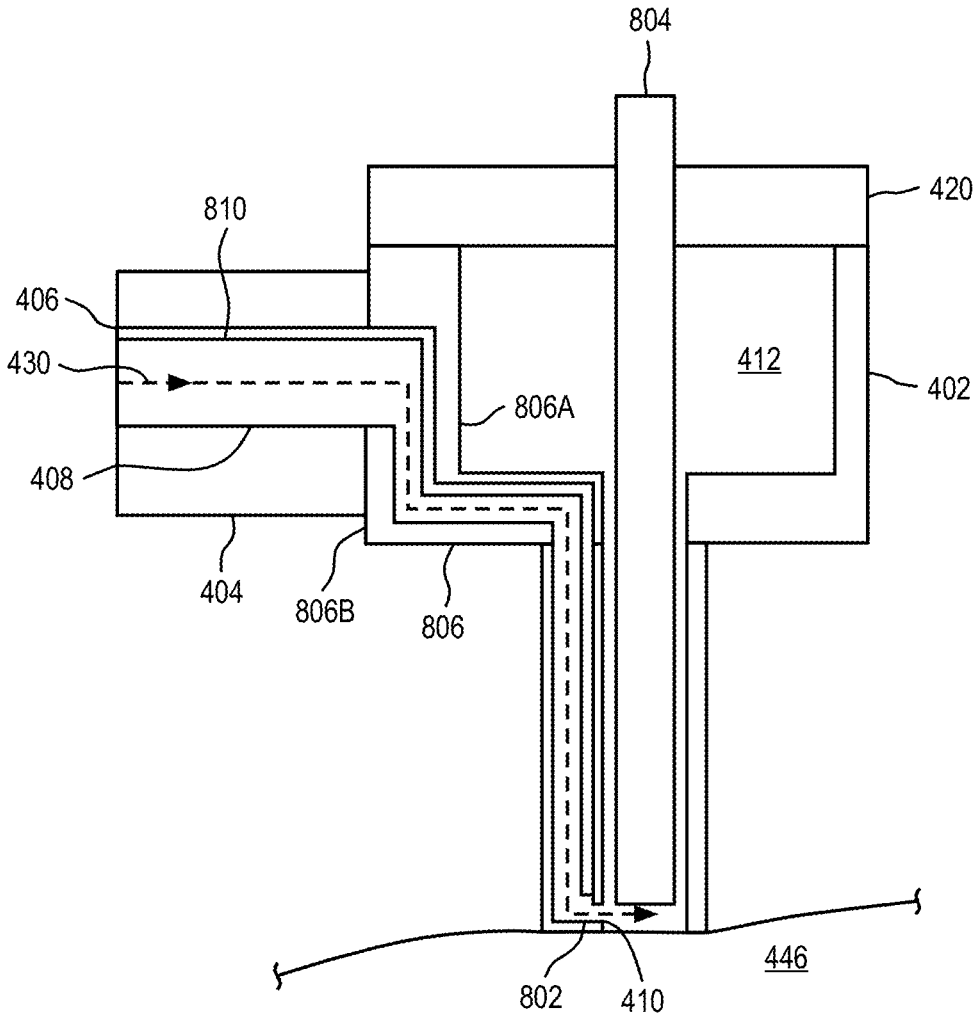
FIG. 8 is a cross-sectional side view of a tool drive and a cannula associated with the trocar of FIG. 3.

FIG. 8 is a cross-sectional side view of a cannula according to another aspect of the invention. The cannula 402 of FIG. 8 is substantially similar to that of FIG. 7 in that it includes a cannula interface 404 that connects to the docking interface (although not shown for case of illustration) as previously discussed. In this aspect, however, the integrated fluid pathway 408 includes a nozzle 802 for cleaning a surgical tool or instrument 804 inserted through the cannula 402. Representatively, similar to the previously discussed configurations, the fluid pathway 408 in the cannula interface 404 extends from fluid port 406 (e.g., facing the docking interface) to a fluid port 410 to the cannula lumen 412. The fluid port 410 to the cannula lumen 412, however, is positioned near the end of the cannula 402 so that when a fluid is transmitted through pathway 408 and out fluid port 410, it is directed toward an end of the instrument 804 positioned within the cannula lumen 412. In some aspects, the pathway 408 may be formed through the cannula interface 404 as previously discussed, and extend down the side wall 806 of cannula 402, to fluid port 410. For example, pathway 408 may include a portion that is formed by a channel between an interior surface 806A (e.g., a surface defining cannula lumen 412) and an exterior surface 806B (e.g., a surface facing the ambient environment) of cannula 402. The fluid port 410 to the cannula lumen 412 may be formed through the interior surface 806A forming the distal end of cannula 402. In this aspect, the pathway 408 may be integrated entirely within the cannula interface 404 and cannula 402. In other aspects, a portion, or portions, of the pathway 408 may be coupled to an exterior surface of the assembly. The end of pathway 408 may further include nozzle 802 to help direct the fluid toward the end of the instrument 804. The nozzle 802 may be any type of nozzle suitable for directing a fluid. For example, the nozzle 802 may be a narrowed portion of pathway 408, or a separate nozzle attached to the end of pathway 408. A fluid (e.g, an insufflation gas) may then be introduced through pathway 408 and out nozzle 802 so that it contacts the end of the instrument 804 at a sufficient flow rate to clean particles or the like off the end of the instrument 804.

In addition, in some aspects, a heating element 810 that is operable to heat the fluid (e.g., insufflation gas) traveling through the pathway 408 may further be provided. The heating element 810 may, for example, be a heated coil or the like that is part of, or otherwise attached to, the insufflation tube that forms the pathway 408. Alternatively, the heating element 810 could be coupled to, or otherwise part of, the cannula interface 404. Heating of the insufflation gas prior to contact with the instrument 804 may help to reduce fogging, for example of a camera or endoscope inserted in the cannula, which can sometimes occur in the absence of a heating element.

Figure 9:
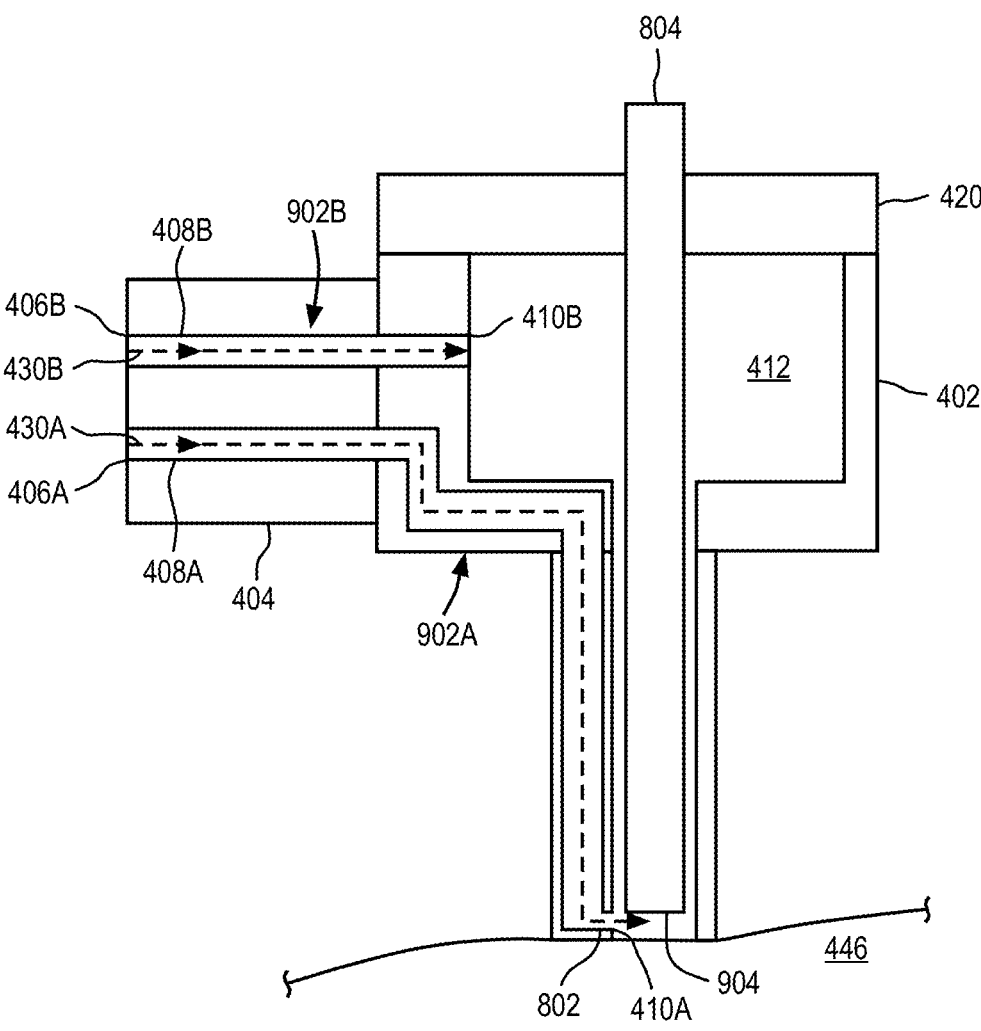
FIG. 9 is a cross-sectional side view of a tool drive and a cannula associated with the trocar of FIG. 3.

FIG. 9 is a cross-sectional side view of a cannula according to another aspect of the invention. The cannula 402 of FIG. 9 is substantially similar to that of FIG. 8 in that it includes a cannula interface 404 that connects to the docking interface (although not shown for case of illustration) as previously discussed. In this embodiment, however, cannula interface 404 is shown including two integrated fluid pathways 902A and 902B. Pathway 902B is substantially similar to pathway 408 as discussed in reference to FIG. 8 and includes the pathway 408A extending between a fluid port 406A (e.g., facing the docking interface) and a fluid port 410A at the end of the cannula 402. The additional fluid pathway 408B is the same as the pathway 408 discussed in reference to FIG. 4-FIG. 7. Representatively, pathway 408B extends from fluid port 406B facing the docking interface to fluid port 410B near the proximal end of the cannula lumen 412 (e.g., the end that receives the surgical instrument). Similar to the previously discussed dual pathway configurations, fluid flow can be switched between pathways 408A-B as desired. In this configuration, however, since pathway 408A can introduce a fluid toward the end of an instrument 804 within cannula 402, the fluid flow is used for insufflation or cleaning of the instrument. The selection of the different operations could be triggered by the operator or automatically depending on whether the instrument 804 is retracted into the cannula 402 so that the instrument tip 904 is near the nozzle 802. It should further be recognized that instrument 804 could be any instrument that may be inserted through the cannula of a trocar during a surgical procedure. For example, the instrument could be an endoscope and the fluid from the nozzle 802 can be used to clean particles off the end of the endoscope after a surgical procedure. In other aspects, the instrument could be a camera and the fluid from the nozzle 802 can be used to remove particles from the camera lens to improve image quality for the viewer.

It should further be understood that although multiple fluid pathways (e.g., pathways 212, 408, 602A-B, 902A-B) associated with a single robotic arm (e.g., arm 104) and cannula (e.g., cannula 402) of the surgical robotic system 100 are described, it is further contemplated that any number of the robotic arms and cannulas of the surgical robotic system 100 may include fluid pathways discussed herein. For example, at least two robotic arm/cannulas of the system 100 may include fluid pathways, and the flow of fluid through each of the pathways may be cooperatively controlled to achieve the desired insufflation, smoke evacuation, and/or particulate removal relative to the associated surgical cavity. For example, system 100 may include one robotic arm/cannula with one pathway coupled to a surgical insufflator and another robotic arm/cannula with another pathway coupled to the surgical insufflator. During operation, one of the pathways of one of the arm/cannula assemblies may be used to introduce a fluid (e.g, insufflation gas) into the surgical cavity while the pathway associated with the other arm/cannula assembly may be used to remove the fluid, smoke, particulate or the like, from the cavity.

In addition, since the surgical insufflator is integrated with, or part of, the surgical robot system 100, the insufflator itself can communicate with robot components of system 100 to robotically control fluid input/output at the surgical site. For example, during surgery, the system detects that it is operating an instrument that creates smoke, such as an energy device. In response, the system can automatically signal to the surgical insufflator to engage in a smoke evacuation operation and remove smoke from the cavity. The system may detect operation of the energy emitter based on an input command by the user, or command by the controller based on a processing protocol input, or a sensor associated with the energy device that emits a signal when in operation, or some other detection mechanism. For example, the controller and/or processor may detect that an energy emitter has been actuated and send a signal to the pump to turn on/off a smoke evacuation operation, turn on/off fluid inlet, or other operation to automatically achieve a desired insufflation, fluid inflow/outflow or particulate evacuation operation.

In still further aspects, the instrument could include a camera (e.g., an endoscope camera), which can take images that may show smoke or particles within the surgical cavity. In this aspect, computer vision may be used to process the camera images and determine smoke is present and needs to be evacuated. In response, the controller could signal to the surgical insufflator to transition to the smoke evacuation mode to remove smoke from the cavity.

Figure 10:
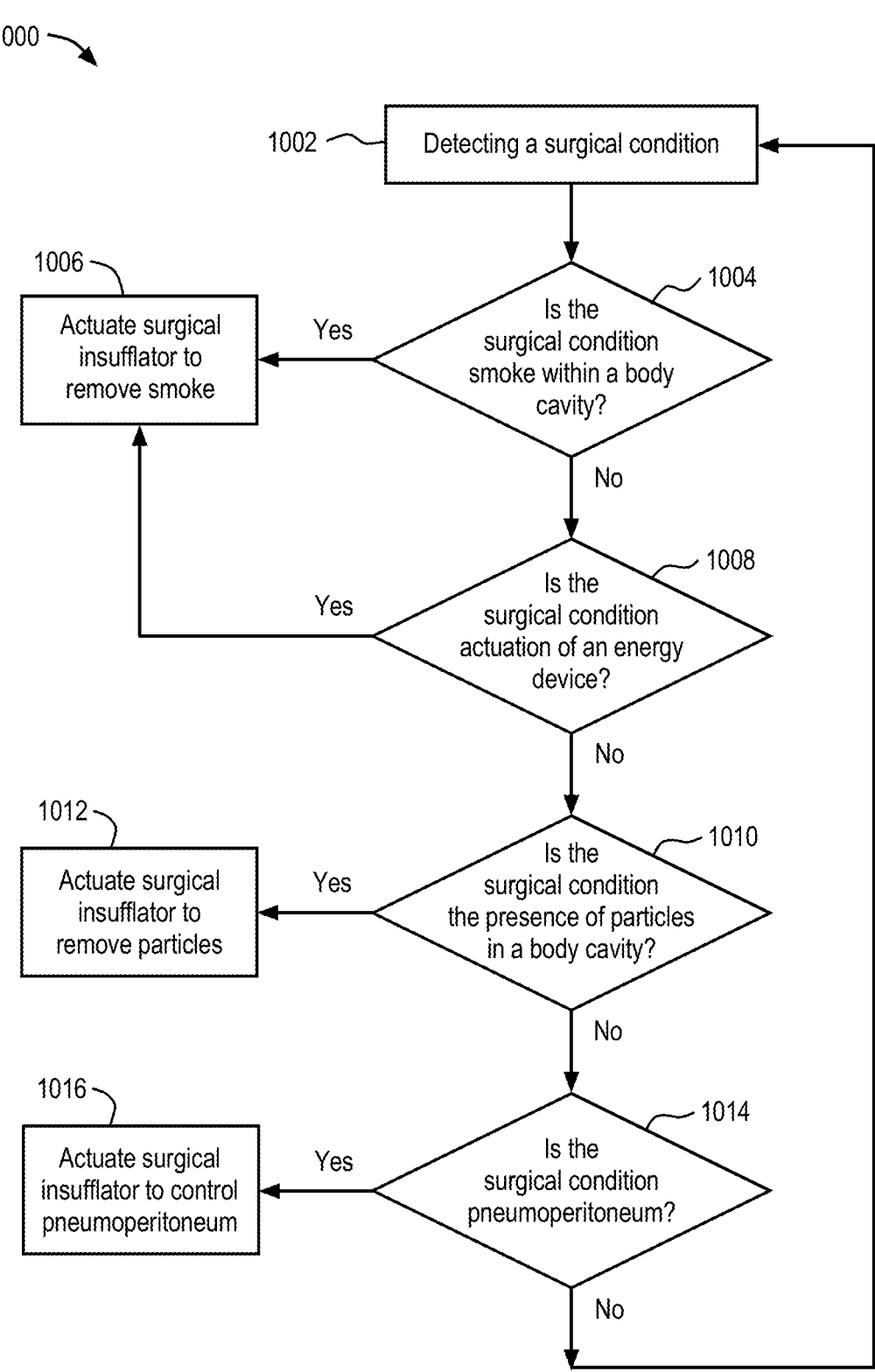
FIG. 10 is a block diagram of an exemplary processing operation of a surgical robotic system, in accordance with an embodiment.

The different fluid input/output operations described herein may therefore be manually controlled by a user (e.g., by a bedside operator 108; or remote surgeon 109) or robotically, automatically, or otherwise dynamically, controlled based on a detected surgical condition. FIG. 10 is a block diagram of one exemplary process for robotically controlling fluid input/output based on a detected surgical condition. Representatively, process 1000 may include the operation of detecting a surgical condition 1002. The surgical condition may be detected based on a user input, an operation performed during a processing protocol, a signal emitted by a surgical component, a visual analysis, or any other indicator that a surgical condition is present. Once the surgical condition is detected, it is determined whether the surgical condition is one of any number of conditions. Representatively, the process includes determining whether the surgical condition is smoke within a body cavity 1004. This condition may be detected, for example, based on an operation of a surgical instrument or device that is known to emit smoke, such as an energy emitting device, a smoke detection sensor associated with one or more surgical components in the cavity, processing an image showing smoke within the body cavity, or any other mechanism suitable for smoke detection. Once smoke is detected, or a condition suggesting the presence of smoke is detected, a signal is sent to the surgical insufflator to initiate a smoke evacuation function or mode. For example, the surgical insufflator is actuated to cause a flow of fluid through the integrated fluid pathways (e.g., pathways 212, 408) away from the body cavity, which in turn, will evacuate the smoke from the cavity, at operation 1006. In addition, in the case where the surgical system includes multiple fluid pathways and/or multiple arm/cannula assemblies, the surgical insufflator may cause fluid to flow (e.g., an insufflation gas) through a pathway associated with one arm/cannula assembly to the body cavity to push the smoke toward another fluid pathway which may be in the same arm/cannula assembly or associated with another arm/cannula assembly. The surgical insufflator causes the other fluid pathway to have a reverse direction of fluid flow and draw the fluid away from the body cavity. If, however, smoke is not detected at operation 1004, the process continues on and determines if the surgical condition is actuation of an energy device at operation 1008. Since operation of an energy device is known to cause smoke, the process then continues to the smoke evacuation operation 1006. If, on the other hand, actuation of an energy device is not detected at operation 1008, the process continues to operation 1010 to determine if particles are present in the body cavity. The presence of particles may be detected visually, based on a known operation that generates particles, a detected instrument blockage caused by particles, or another indicator of the presence of particles. If particles are detected, the surgical insufflator is caused to engage in a particle removal operation or mode at operation 1012. The particular removal operation or mode may involve the insufflator causing an outflow of fluid through the integrated pathways and away from the body cavity (e.g., to evacuate the particles). Alternatively, where the particles are detected on a surgical instrument or device, such as the endoscope, the insufflator may cause an inflow of fluid to the body cavity to drive (e.g., blow) the particles off of the device. If, however, particles are not detected at operation 1010, the process continues on and determines if the condition relates to pneumoperitoneum at operation 1014. Pneumoperitoneum refers to the condition where insufflation gas (e.g., carbon dioxide) is introduced into the peritoneal cavity (e.g., surgical site) to increase the size of the cavity. The gas causes an increase in pressure within the cavity, and this pressure can be monitored using pressure sensors associated with the insufflator and/or surgical system. For example, the pressure sensors can detect a pressure level (or changes in pressure level) within the body cavity and this information can be used to monitor whether the pressure level is within a desired range, or otherwise meets a desired threshold level suitable for the surgical procedure. If a pneumoperitoneum related condition is detected, for example, a change in pressure level within the surgical site or cavity, the surgical insufflator is then actuated and used to control and/or monitor pneumoperitoneum within the body cavity at operation 1016 so that desired conditions for the surgical operation are consistently maintained. For example, if the pressure level (or level of gas within the cavity) are lower than desired, the surgical insufflator may increase the surgical insufflator may cause a flow of insufflation gas through the integrated pathway(s) to the body cavity. If the pressure level is higher than desired, the surgical insufflator may decrease the flow of insufflation gas to the body cavity. If none of these surgical conditions are determined, process 1000 returns to operation 1002 and continues to determine whether a surgical condition requiring actuation of the surgical insufflator is found. It should further be understood that any one or more of the previously discussed conditions 1004, 1008, 1010, 1014 may be detected and/or monitored at the same or different times, and actuation of the surgical insufflator in response to these conditions as described in operations 1006, 1012, 1016 may also be performed at the same or different times.

Figure 11:
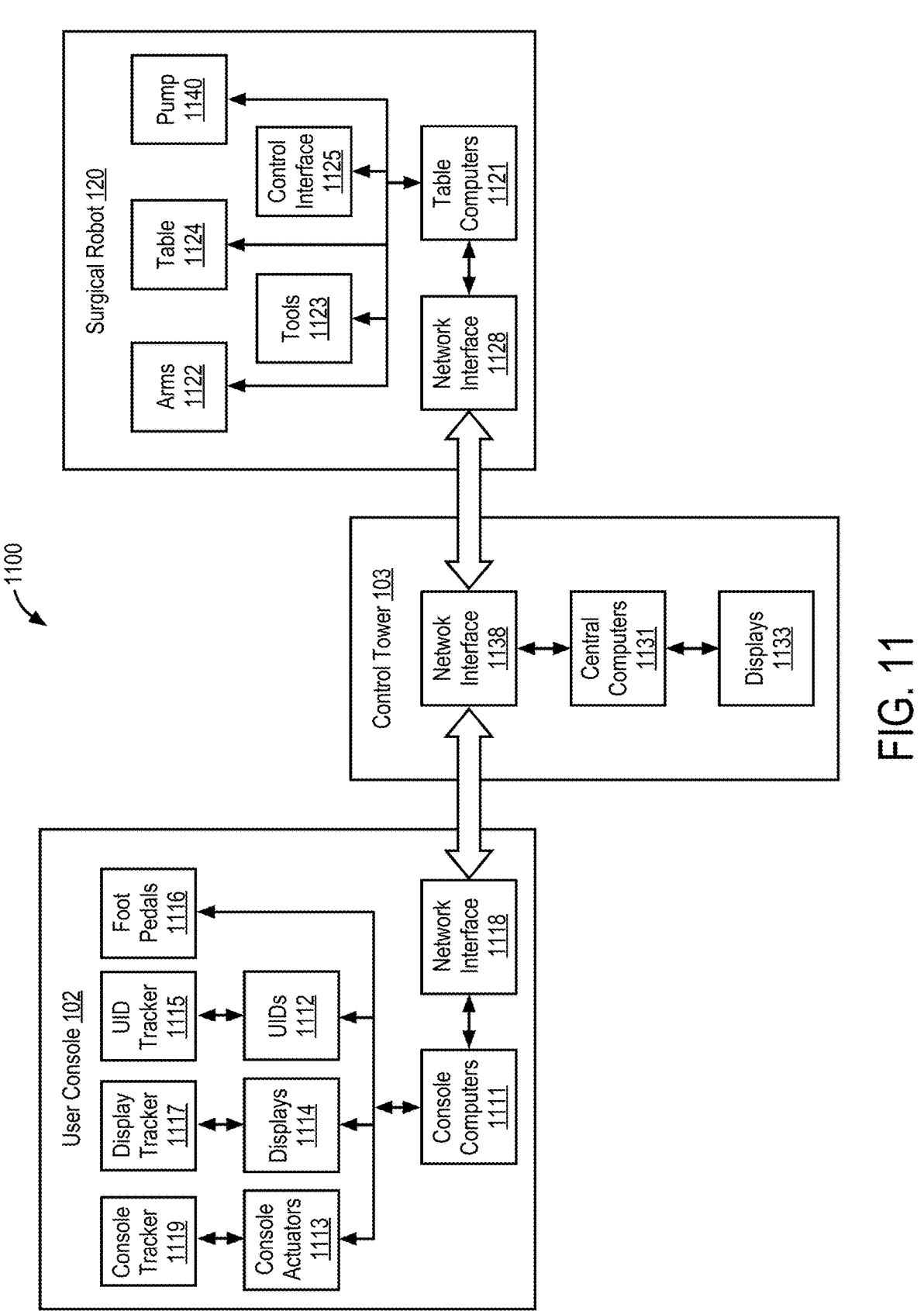
FIG. 11 is a block diagram of a computer portion of a surgical robotic system, in accordance with an embodiment.

FIG. 11 is a block diagram of a computer portion of a surgical robotic system, which is operable to implement the previously discussed operations, in accordance with an embodiment. The exemplary surgical robotic system 1100 may include a user console 102, a surgical robot 120, and a control tower 103. The surgical robotic system 1100 may include other or additional hardware components; thus, the diagram is provided by way of example and not a limitation to the system architecture.

As described above, the user console 102 may include console computers 1111, one or more UIDs 1112, console actuators 1113, displays 1114, foot pedals 1116, console computers 1111 and a network interface 1118. In addition, user console 102 may include a number of components, for example, a UID tracker(s) 1115, a display tracker(s) 1117 and a console tracker(s) 1119, for detecting various surgical conditions required for operation of the system (e.g., UID orientation, orientation of the surgeon relative to the display, orientation the console seat, etc). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1113 based on user input or stored configurations by the console computers 1111. The user may perform robot-assisted surgeries by controlling the surgical robot 120 using one or more master UIDs 1112 and foot pedals 1116. Positions and orientations of the UIDs 1112 are continuously tracked by the UID tracker 1115, and status changes are recorded by the console computers 1111 as user input and dispatched to the control tower 103 via the network interface 1118. Real-time surgical video of patient anatomy, instrumentation, and relevant software apps can be presented to the user on the high resolution 3D displays 1114 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 11, the control tower 103 may include central computers 1131 including at least a visualization computer, a control computer, and an auxiliary computer, various displays 1133 including a team display and a nurse display, and a network interface 1118 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/ monitoring and interacting with cloud-based web services.

The surgical robot 120 may include an operating table 1124 with a plurality of integrated robotic arms 1122 that can be positioned over the target patient anatomy. A suite of compatible tools 1123 can be attached to or detached from the distal ends of the arms 1122, enabling the surgeon to perform various surgical procedures. In addition, a pump 1140 for controlling fluid inflow/outflow of the integrated pathways of the arms 112, as previously discussed, may further be included. The surgical robot 120 may also comprise control interface 1125 for manual or automated control of the arms 1122, pump 1140, table 1124, and tools 1123.

The control interface can include items such as, but not limited to, remote controls, buttons, panels, and touch-screens. Other accessories such as trocars (sleeves, seal cartridge, and obturators) and drapes may also be needed to perform procedures with the system. In some variations, the plurality of the arms 1122 includes four arms mounted on both sides of the operating table 1124, with two arms on each side. For certain surgical procedures, an arm mounted on one side of the table can be positioned on the other side of the table by stretching out and crossing over under the table and arms mounted on the other side, resulting in a total of three arms positioned on the same side of the table 1124. The surgical tool can also comprise table computers 1121 and a network interface 1118, which can place the surgical robot 120 in communication with the control tower 103.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A surgical robotic system comprising:
a robotic arm having an insufflation tube coupled thereto;
a tool drive coupled to a distal end of the robotic arm and having a docking interface through which the insufflation tube extends; and
a cannula interface configured to be received by the docking interface to couple a cannula to the tool drive, the cannula interface having an integrated fluid pathway in communication at a proximal end with the insufflation tube and at a distal end with an interior lumen of the cannula.

2. The surgical robotic system of claim 1 wherein the integrated fluid pathway is a channel formed within the cannula interface between a fluid port at a proximal end of the cannula interface and a fluid port at a distal end of the cannula interface, and the channel is dimensioned to allow transmission of an insufflation gas between the insufflation tube and the interior lumen of the cannula.

3. The surgical robotic system of claim 1 wherein the insufflation tube comprises a proximal end coupled to a surgical insufflator and a distal end coupled to the proximal end of the integrated fluid pathway.

4. The surgical robotic system of claim 1 wherein the interior lumen of the cannula is dimensioned to receive a surgical tool.

5. The surgical robotic system of claim 1 further comprising a filter in communication with the integrated fluid pathway such that an insufflation gas transmitted through the insufflation tube to the integrated fluid pathway passes through the filter.

6. The surgical robotic system of claim 5 wherein the filter is integrated into a sterile adapter positioned between the tool drive and the cannula interface.

7. The surgical robotic system of claim 6 further comprising a sealing element integrated into the sterile adapter to seal the filter between the tool drive and the cannula interface and prevent leakage of the insufflation gas.

8. The surgical robotic system of claim 1 wherein the integrated fluid pathway is a first fluid pathway and the insufflation tube is a first insufflation tube, and the surgical robotic system further comprises a second fluid pathway coupled to a second insufflation tube.

9. The surgical robotic system of claim 8 further comprising a valve coupled to at least one of the first fluid pathway or the second fluid pathway to control a flow of a fluid through the first fluid pathway or the second fluid pathway.

10. The surgical robotic system of claim 1 further comprising a nozzle coupled to the integrated fluid pathway, wherein the nozzle is configured to direct an insufflation gas flowing through the integrated fluid pathway toward a surgical tool positioned within the interior lumen of the cannula.

11. The surgical robotic system of claim 1 wherein the insufflation tube is enclosed within an outer shell of the robotic arm.

12. The surgical robotic system of claim 1 wherein the insufflation tube is mechanically attached to an outer surface of an outer shell of the robotic arm.

13. A surgical robotic system comprising:

a surgical robotic assembly comprising:

a robotic arm comprising an insufflation pathway having a proximal portion coupled to a surgical insufflator and a distal portion, a tool drive coupled to a distal portion of the robotic arm and having a docking interface through which the distal portion of the insufflation pathway extends, and a cannula interface configured to be received by the docking interface to couple a cannula to the tool drive, the cannula interface having an integrated fluid pathway in communication at a proximal portion with the insufflation pathway and at a distal portion with an interior lumen of the cannula dimensioned to receive a surgical tool; and a processor communicatively coupled to the surgical robotic assembly and the surgical insufflator, the processor operable to control an operation of the surgical insufflator based on a detected surgical condition.

14. The surgical robotic system of claim 13 wherein the detected surgical condition comprises a presence of smoke within a surgical site; and the operation controlled by the processor is a smoke evacuation function of the surgical insufflator.

15. The surgical robotic system of claim 14 wherein the smoke evacuation function comprises actively evacuating smoke through the insufflation pathway while maintaining pneumoperitoneum at the surgical site.

16. The surgical robotic system of claim 14 wherein the integrated fluid pathway is a first fluid pathway and the insufflation pathway is a first insufflation pathway, and the surgical robotic assembly further comprises a second fluid pathway and a second insufflation pathway that are not fluidly coupled to the surgical insufflator, and the smoke evacuation function comprise passively evacuating smoke through the second fluid pathway and second insufflation pathway.

17. The surgical robotic system of claim 14 wherein the robotic arm is a first robotic arm and the insufflation pathway is a first insufflation pathway, the surgical robotic system further comprising a second robotic arm and a second insufflation pathway integrated with the second robotic arm, and the smoke evacuation function comprises introducing a flow of fluid to a surgical cavity through the first insufflation pathway and evacuating smoke from the surgical cavity using the second insufflation pathway.

18. The surgical robotic system of claim 13 wherein the detected surgical condition comprises activation of an energy device within a surgical site; and the operation controlled by the processor is a smoke evacuation function of the surgical insufflator.

19. The surgical robotic system of claim 13 wherein the detected surgical condition comprises a presence of particles within a surgical site; and the operation controlled by the processor is a particle removal function of the surgical insufflator.

* * * * *